United States Patent [19]
Egolf et al.

[11] Patent Number: 5,078,687
[45] Date of Patent: Jan. 7, 1992

[54] CATHETER WITH BACKFLOW RESTRICTION

[75] Inventors: William Egolf; Michael O'Neil, both of Palm Harbor; Mark Panzera; Joseph Chang, both of Tampa, all of Fla.

[73] Assignee: Critikon, Inc., Tampa, Fla.

[21] Appl. No.: 567,419

[22] Filed: Aug. 14, 1990

Related U.S. Application Data

[63] Continuation of Ser. No. 353,276, May 17, 1989, abandoned.

[51] Int. Cl.$^5$ .............................................. A61M 5/178
[52] U.S. Cl. ...................................... 604/164; 604/165
[58] Field of Search .................... 604/164–170, 604/192, 198, 239, 263, 264, 280, 283, 900; 128/768

[56] References Cited

U.S. PATENT DOCUMENTS

| | | | |
|---|---|---|---|
| 3,094,122 | 6/1963 | Gauthier et al. | 128/221 |
| 3,388,703 | 6/1968 | Bowes | 128/214.4 |
| 3,406,685 | 10/1968 | May | 128/214.4 |
| 3,540,447 | 11/1970 | Howe | 128/221 |
| 4,249,541 | 2/1981 | Pratt | 128/753 |
| 4,317,445 | 3/1982 | Robinson | 128/214.4 |
| 4,547,194 | 10/1985 | Moorehead | 604/283 |
| 4,588,398 | 5/1986 | Daugherty et al. | 604/265 |
| 4,629,450 | 12/1986 | Suzuki et al. | 604/164 |
| 4,772,267 | 9/1988 | Brown | 604/263 |
| 4,781,703 | 11/1988 | Walker et al. | 604/264 |
| 4,840,622 | 6/1989 | Hardy | 604/264 |

*Primary Examiner*—John D. Yasko
*Assistant Examiner*—A. Gutowski
*Attorney, Agent, or Firm*—Paul A. Coletti

[57] ABSTRACT

An over-the-needle catheter assembly is provided in which a restriction of the inner diameter of the catheter tube is formed in the proximity of the needle hub. The restriction is formed by heating a portion of the catheter tube to the softening point of the catheter material, stretching the catheter tube to cause the heated portion of the catheter tube to tighten about an inner needle or mandril, then releasing the stretching force to allow the stretched portion to relax, leaving a small gap between the inner wall of the catheter tube and the outer diameter of the insertion needle. The small gap is preferably sized to be on the order of the size of the diameter of blood cells to restrict the flow of liquids past the restriction and into the catheter hub.

7 Claims, 4 Drawing Sheets

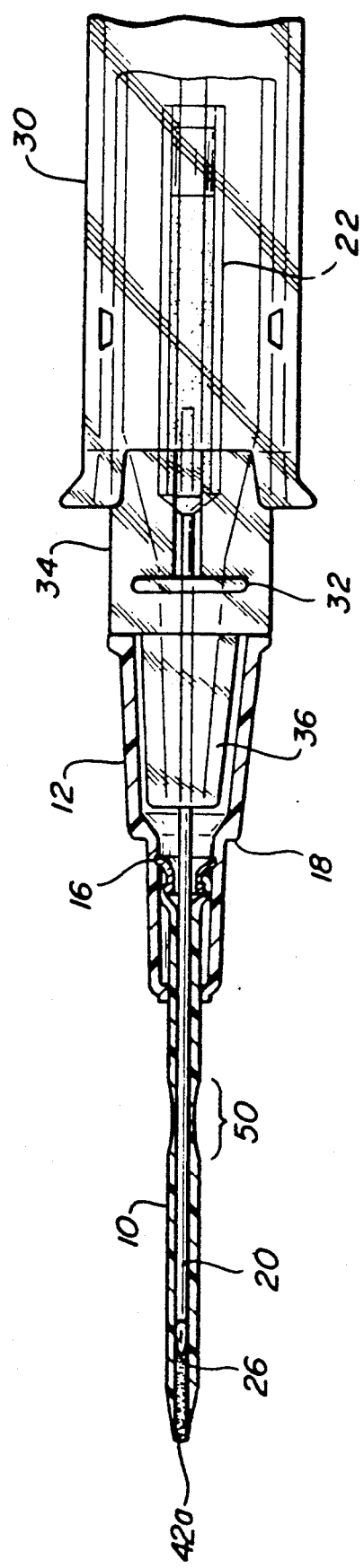

CATHETER WITH BACKFLOW RESTRICTION

This is a continuation of application Ser. No. 353,276, filed May 17, 1989, now abandoned.

This invention relates to I.V. catheters and, in particular, to the prevention of blood backflow and blood pooling which could result in inadvertent contact with blood during the use of such catheters.

Luther et al. U.S. Pat. No. 4,762,516 and U.S. patent application Ser. No. 335,472, filed Apr. 10, 1989, describe I.V. catheters with needle guards that are designed to protect medical personnel from inadvertent injury caused by needle sticks subsequent to use of the catheter needle. Such inadvertent needle sticks can result in infection by diseases borne by the blood of the patient from whose vascular system the needle has been previously withdrawn. The catheters described in this patent and patent application prevent inadvertent needle sticks by covering the needle tip with a needle guard extending from the needle hub as the needle is withdrawn from the patient's body.

It is not only desirable to protect medical personnel from the hazards of inadvertent needle sticks, but it is further desirable to provide protection from any contact with a patient's blood. Even in the use of one of the aforementioned catheters with needle guards, it is possible for medical personnel to come into contact with a patient's blood due to undesired leakage of blood from the catheter. During insertion of the needle into the vascular system of the patient, the clinician administering the catheter will try to locate the tip of the needle in a vein or artery of the patient. When the needle tip is properly located, there will be a small flow or flash of blood through the hollow needle and into the flash chamber at the proximal end of the needle. The clinician will note this presence of blood in the flash chamber as an indication of proper needle placement. The clinician can then advance the catheter into the vascular system and withdraw the needle from the patient, leaving the catheter cannula in place in the blood vessel.

As the needle tip moves to a location proximal the distal end of the catheter, blood will flow under venous or arterial pressure into the catheter and into the hollow needle. However blood may also enter the annular space between the outer wall of the needle and the inner wall of the catheter cannula. The flow of blood in this space toward the catheter hub is herein referred to as backflow. Normally, backflow of blood is of little concern, because the catheter hub is usually quickly connected to a tubing set once the needle is withdrawn from the catheter. However, in the aforementioned catheters with needle guards, the distal nose of the needle guard occupies the catheter hub prior to complete withdrawal of the needle. As the needle guard is extended along the length of the needle toward the needle tip, its extension will carry the catheter hub to simultaneously thread the catheter into the vein or artery of the patient. The termination of this motion will eject the catheter hub from the nose of the guard when the guard reaches it full extension. Thus, if blood backflow into the catheter hub occurs Prior to ejection of the catheter hub from the nose of the guard, the needle guard will be contaminated with the patient's blood prior to the release of the catheter hub. It would be desirable to Prevent this contamination so that contact by medical personnel with blood on the nose of the needle guard will be prevented.

In accordance with the Principles of the present invention, a catheter is provided which deters the backflow of blood between the insertion needle and the catheter cannula. The catheter hub and cannula are formed in a conventional manner, then mounted on the insertion needle or a mandril of a gauge similar to that of the needle. The cannula is then heated in the proximity of the catheter hub to a temperature which is at least equal to the softening temperature of the cannula material. As the cannula is heated it is pulled slightly in the longitudinal direction. This pulling stretches the heated portion of the cannula tightly around the mandril or needle. The stretched cannula is held momentarily as the heat source is removed, then released. When the cannula is released, it relaxes slightly both longitudinally and radially to create a tiny annular space between the cannula and the mandril or needle. Through optimization of the stretching parameters the resultant tiny space is calibrated relative to the size of blood cells so as to Prevent their Passage through the restriction thus formed by the cannula. The optimization further minimizes the friction between the restriction and the needle as the needle is withdrawn from the catheter during us of the catheter and needle. The restriction thus substantially reduces blood backflow between the needle and the cannula while creating only a negligible increase in frictional forces during withdrawal of the needle from the cannula.

In the drawings:

FIG. 3 illustrates a catheter with a restriction formed in accordance with the principles of the present invention;

Figure 1:
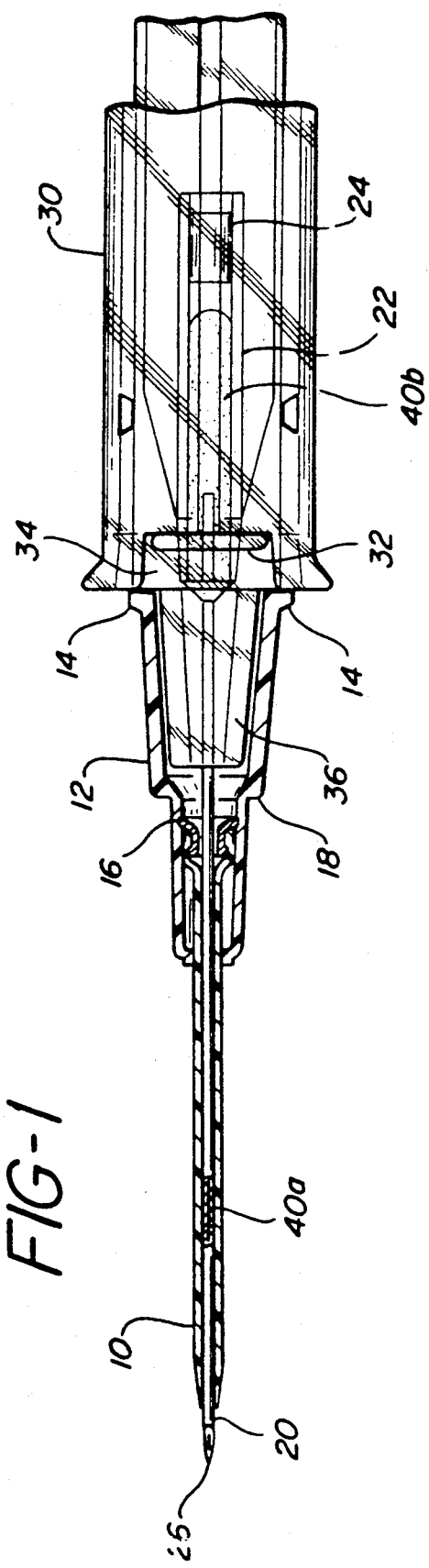
FIG. 1 illustrates a catheter and needle assembly with blood flow to the flash chamber in the needle hub.

Referring first to FIG. 1, a catheter and needle with a needle guard is shown, which may be constructed as described in the aforementioned patent and patent application. The assembly includes a catheter cannula 10 which is connected to a catheter hub 12. A luer lock 14 is formed at the proximal end of the catheter hub 12. The cannula is attached to the hub 12 by the press fit of a flared metal sleeve 16 inside the proximal end of the cannula inside the hub 12, as described in Lemieux U.S. Pat. No. 4,191,185.

A hollow metal insertion needle 20 has a pointed distal end 26. The proximal end of the needle 20 is adhesively attached to the distal end opening of a flash chamber 22, which is mounted inside a needle hub or housing 30. The mounting of the flash chamber to the housing is not visible in the drawing, and comprises a longitudinal, rail-like extension from the interior of the housing to the outside of the flash chamber. The proximal end of the flash chamber is plugged by a porous plug 24 as described in U.S. patent application Ser. No. 221,579, filed July 20, 1988. The porous plug vents air from the flash chamber as the chamber fills with blood, and the pores of the plug are of insufficient size to permit blood to pass therethrough.

Slideably mounted inside the needle housing 30 is a needle guard 34, shown in its retracted Position in FIG. 1. The interior of the needle guard is hollow to accommodate the flash chamber therein. The needle guard has a longitudinal opening or slot in one side through which the mounting extension of the flash chamber passes. The distal end or nose 36 of the needle guard is tapered and contains an aperture for Passage of the needle through the guard as the guard is extended. The catheter hub 12 mounts on the nose 36 of the needle guard and travels on the nose as the guard is extended until the catheter and hub are ejected when the guard is fully extended over the needle.

FIG. 1 also shows the desired flow of blood into the catheter assembly when the needle tip is properly located in a blood vessel. Blood will flow under arterial or venous pressure through the hollow needle as shown at 40a and into the flash chamber 22 as shown at 40b.

Figure 2:
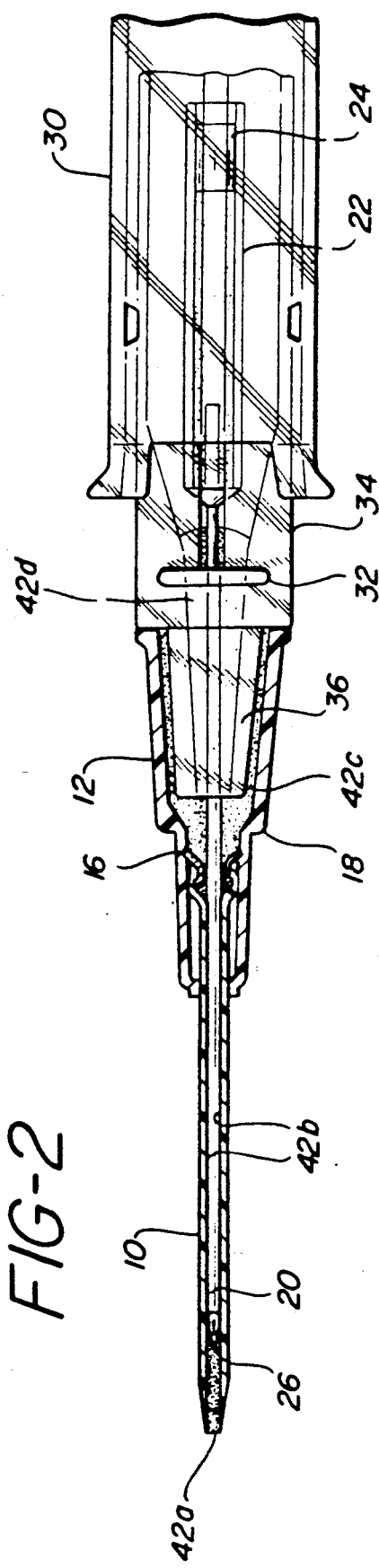
FIG. 2 illustrates the problem of blood backflow and blood pooling at the nose of the needle guard.

FIG. 2 shows the relative position of the components of the catheter assembly after the needle tip has been located in a blood vessel. At this time the needle guard 34 is extended by the clinician by pressing the guard's push-off tab 32 in the distal direction. This motion causes the needle tip 26 to retract relative to the distal end of the catheter 10 to the position shown in FIG. 2, which is referred to as "hooding" of the needle tip inside the distal end of the catheter. When the needle tip 26 is hooded, blood flows into and fills the distal end of the catheter as indicated at 42a. But in addition to the desired flow of blood through the hollow needle as shown in FIG. 1, blood may also flow into and through the small annular space between the outside of the needle and the inside of the catheter cannula, as indicated at 42b. This backflow of blood can reach the interior of the catheter hub 12 where blood pooling will occur, as indicated at 42c. This pooling of blood will undesirably contaminate the outside of the needle guard nose 36, and can also flow into the nose of the needle guard as indicated at 42d. It is an object of the present invention to prevent this backflow of blood and pooling of blood around the nose of the needle guard.

FIG. 3 shows a catheter constructed in accordance with the principles of the present invention which includes a restriction 50 formed in the catheter cannula 10 in the vicinity of the catheter hub 12. The restriction 50 comprises a reduction of the inside diameter of the catheter cannula to a size that closely fits around the outer diameter of the needle 20. As FIG. 3 shows, blood will still flow into the distal end of the catheter cannula 10 and around the hooded tip 26 of the needle, and may even begin to backflow through the annular space between the needle and the cannula. But when the backflow of blood reaches the restriction 50 the relatively tight fit of the cannula and the needle deters further blood backflow into the catheter hub. This substantially prevents contamination of the needle guard nose by blood pooling around the nose 36 of the needle guard inside the catheter hub.

Figure 4A:
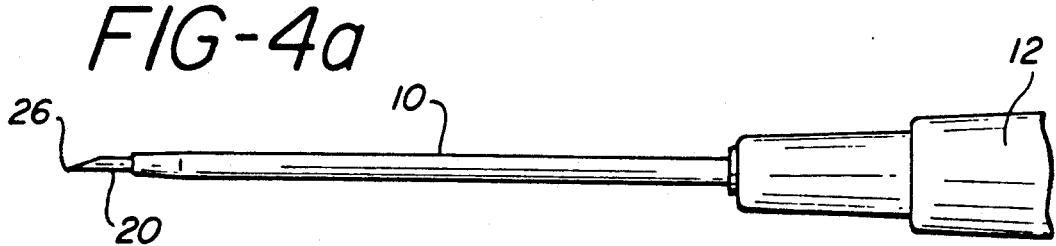
FIGS. 4a–4d illustrate the steps involved in the formation of the restriction of FIG. 3.
Figure 4B:
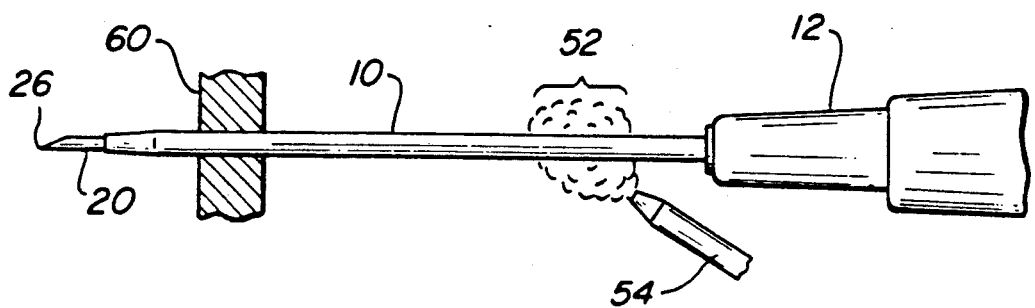
Figure 4C:
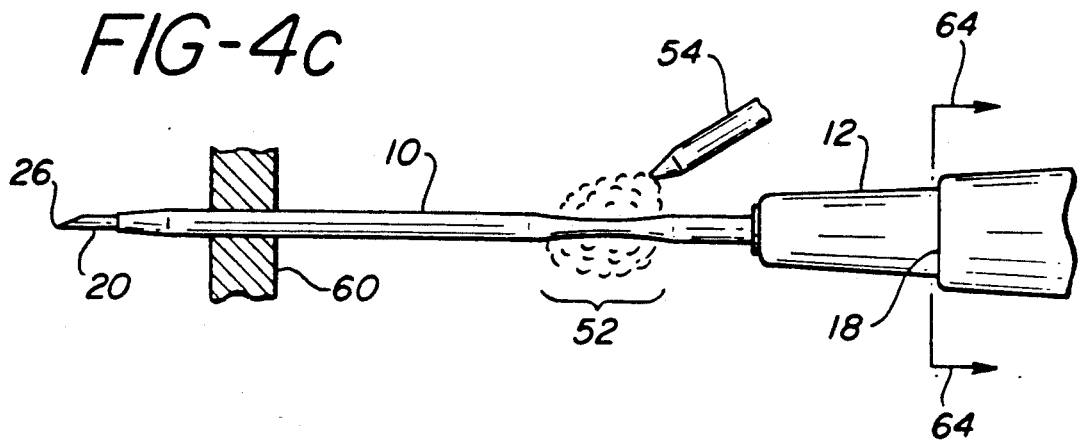
Figure 4D:
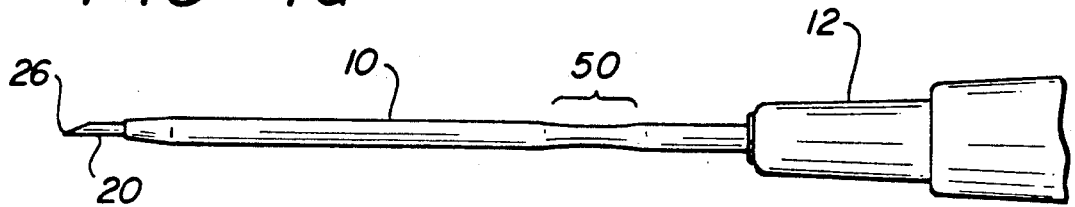

The restriction 50 is formed as illustrated by FIGS. 4a–4d and 5a–5c. FIG. 4a shows the catheter cannula 10 and hub 12 mounted on the hollow needle 20. The restriction 50 is preferably formed when the component parts of the catheter are assembled as shown in FIG. 4a. However, the restriction may also be formed by mounting the catheter and catheter hub on a mandril of substantially the same gauge as that of the needle. Forming the restriction on the needle itself will generally result in a reduction of assembly steps for the device.

The catheter cannula 10 is normally made of a polymer such as tetrafluoroethylene, which is commercially available under the tradename Teflon TM. Other polymers approved for use in medical devices may also be used. In any case, the first step is to preheat the cannula at the point 52 where the restriction is to be formed. The cannula is preheated to the melting point of the cannula material, which for Teflon is 470° F. While the cannula is preheated the catheter is clamped near its distal end by a clamp 60 made of a soft material such as a polyurethane pad or silicone rubber.

The present inventors have employed several different techniques to heat the catheter cannula. One is to insert the cannula through a quarter inch diameter center hole in a disc-like hot plate s that the hot plate surrounds the point 52 where the restriction is to be formed. The cannula does not touch the hot plate, but is heated by the convective flow of air from the hot plate, which is heated to a temperature in the range of 520° F. to 575° F., and preferably about 520° F. A second, Preferred technique is to direct a stream of air heated to 550° F. to 650° F. and preferably about 600° F. at the cannula from a pencil-tip hot air gun or other source, as indicated at 54 in FIG. 4b. The turbulence caused by the stream of air from such a source will substantially uniformly heat the air surrounding the cannula to the melting point of the cannula material. The stream of heated air may be directed at a deflector plate in the vicinity of the restriction region to enhance its turbulence. Due to the small mass of the catheter, this preheating requires only a short period of time. In the case of the hot plate, preheating takes approximately 5 to 8 seconds. In the case Of the pencil-tip hot air source, preheating takes only 0.5 to 1.5 seconds, with longer times being required to heat larger size (i.e., small gauge number) catheters.

At the end of the preheating period, the cannula 10 is stretched a predetermined distance. This may be done by grasping the catheter hub 12 and pulling on the clamp 60. Preferably the clamp 60 is fixed in position and an annular bracket fitted against the shoulder 18 of the catheter hub 12 pulls the hub as indicated by arrows 64 in FIG. 4c. In a constructed embodiment of the present invention using a 20 gauge Teflon TM catheter, the cannula was stretched a distance of 0.210 inches when using the hot plate for heating. The stretching distance for a variety of catheter gauges constructed ranged from 0.15 to 0.30 inches. When using the pencil-tip hot air source, the cannula is stretched a distance of sixty thousandths of an inch for a 20 gauge catheter. Other catheter gauges ranged from 0.02 to 0.1 inches. This stretching will cause the heated region of the cannula to tightly contract around the inner needle or mandril. After the cannula has been stretched it is held in the stretched position for a predetermined period of time. In the case of use of the hot plate, the stretched position is held for 2 to 5 seconds. In the case of the pencil-tip hot air source the position is held for 0.1 to 1.0 seconds. The cannula is then removed from the hole in the hot plate and allowed to cool. In the instance of the Pencil-tip hot air source, the stream of hot air is removed from the cannula and the cannula is held in the stretched position for another 0.2 to 1.0 seconds. The stretched cannula is then released and allowed to cool for a few seconds.

When the heat is removed from the cannula and the stretching force released, the cannula material cools and solidifies in a very few seconds due to its small thermal mass. As it cools without the stretching force the cannula material will also relax and expand in the longitudinal and radial directions. This relaxing of the material will alleviate the tight fit of the cannula around the needle or mandril, leaving a narrow annular gap between the cannula and the needle or mandril where the restriction is formed. The optimum gap is in the range of 0.2 to 1.0 thousandths of an inch, and is nominally 0.5 thousandths of an inch. The result of stretching and relaxation is also to provide a smooth, aesthetically acceptable transition in catheter diameter between the normal catheter diameter and that of the restriction so as to minimize the possibility of side puncture or skiving upon needle point insertion.

It may be seen that when the hot plate is used in the formation of the restriction, the time to form the restriction is approximately ten seconds. When the pencil-tip hot air source is employed, the time to form the restriction is 3.5 seconds or less, and nominally less than 2 seconds.

Figure 5A:
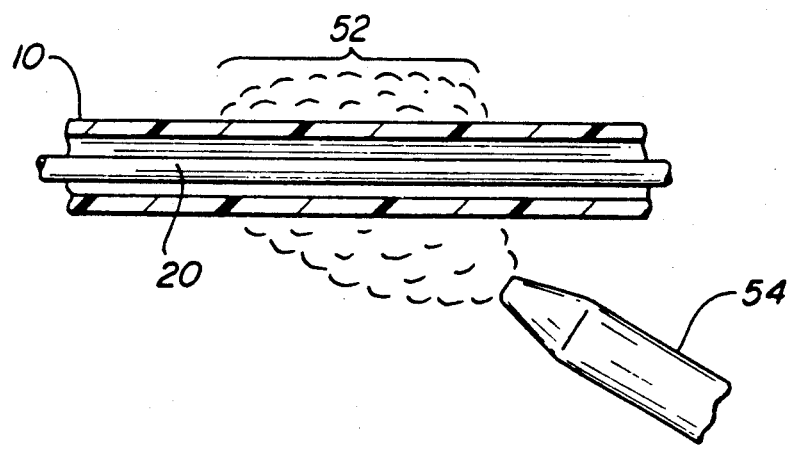
FIGS. 5a–5c are enlarged views of the restriction formed in FIGS. 4a–4d.
Figure 5B:
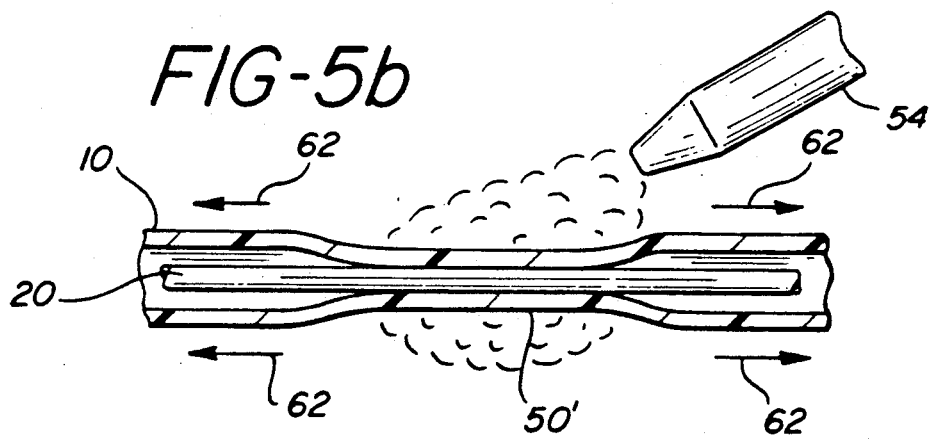
Figure 5C:
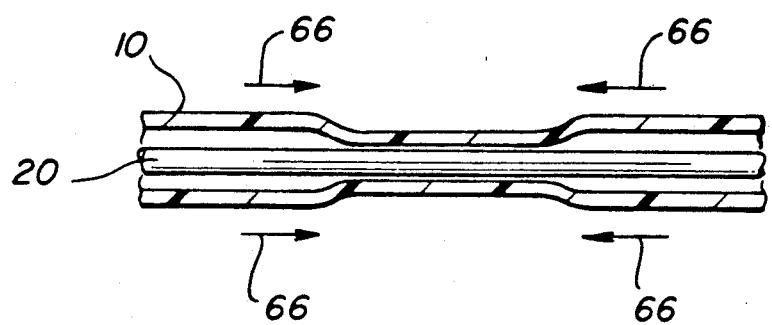

Enlarged views of the formation of the cannula restriction are shown in FIGS. 5a-5c. FIG. 5a shows the catheter cannula 10 and needle 20 at the outset of the preheating step and shows the annular space between the needle and cannula in the region 52 where the restriction is to be formed. FIG. 5b shows the heated cannula 10 drawn tightly around the needle 20 at 50' when the heated cannula is stretched. The arrows 62 indicate the direction of the stretching forces. FIG. 5c illustrates the relaxation of the cannula material occurring after the stretching forces and heat are removed. The cannula relaxes longitudinally as indicated by the arrows 66, and radially to leave the small gap between the inner diameter of the restriction and the outer diameter of the needle. Since the nominal diameter of a red blood cell is approximately 7 microns and the nominal diameter of a white blood cell is approximately 12 microns, a nominal gap of 0.5 thousandths of an inch (12.5 microns) will substantially restrict the flow of blood through the restriction.

In the constructed embodiment of the present invention using a 20 gauge catheter, the restriction 50 is located close to the catheter hub, separated therefrom by a distance of approximately one-eighth of an inch. The restriction itself is approximately one-quarter of an inch in length. The length of a typical catheter tube of an I.V. catheter ranges from one-half inch to one and three-quarters inches. By locating the restriction close to the hub as opposed to near the distal end of the cannula, the restriction is effective during much of the withdrawal time of the needle, and becomes ineffective only when the needle tip is withdrawn to a point proximal the restriction. It is not desirable to locate the restriction immediately adjacent the catheter hub for several reasons. For one, heating the cannula at the hub may also undesirably melt the distal end of the catheter hub. Another reason is that catheter bending or kinking will generally occur where the cannula meets the hub. By locating the restriction away from this jointure, cannula kinking at this point will not be promoted by the restriction.

Constructed embodiments were bench tested to determine the effectiveness of the restriction in preventing backflow. The catheter assemblies were inserted into a source of sugar solution pressurized to 20-30 mm Hg. The catheter needles were then hooded as shown in FIG. 3 and monitored to determine the time at which solution appeared in the catheter hubs. The time of passage until solution backflow appeared in the hubs ranged from a minimum of 12.9 seconds for 18 gauge catheters; 15 seconds for 20 gauge catheters; and over 60 seconds for 22 gauge catheters. The maximum times for backflow to appear in the majority of the catheters tested was in excess of 60 seconds. Similar catheters without the restriction ranged from 1.2 to 8.0 seconds until the backflow problem occurred. This test compares favorably to nominal venous pressures in humans of 5-10 mm Hg., and also compare favorably with the time required to withdraw a needle from a catheter and connect the catheter hub to a tubing set, which is generally well under one minute.

Another factor measured was the increase in force required to withdraw the needle from the cannula with the restriction. The increase in force was compared with the force nominally required to withdraw a needle from the skin of a patient, which is generally in excess of 100 grams. It was found that a restriction of one-quarter inch in length with the nominal gap of 0.5 thousandths of an inch imposed an increase in withdrawal friction of about 15 grams, which is negligible as compared with the usual frictional forces extant during needle withdrawal.

The catheters of the present invention with the restriction in the cannula further permit clinicians to use the catheter needle as a core for restricting backflow while preparing for needle withdrawal, such preparation including placing gauze beneath the catheter, reaching for an injection cap or I.V. line, etc. The restriction will substantially impair blood backflow until the clinician is ready to withdraw the needle, and the needle will be withdrawn into its safety needle guard without significant blood contamination of the nose of the needle guard thus, the incidence of blood contact is minimized.

What is claimed is:

1. An over-the-needle catheter assembly which restricts the backflow of liquid between the inner wall of a catheter tube and an insertion needle comprising:
   an insertion needle attached to a needle hub and having a uniform outer diameter; and
   a catheter tube having a distal tip and a proximal end attached to a catheter hub;
   said needle inserted into said catheter tube, wherein said catheter tube has a nominal inner diameter over a major portion of its length for accommodating the passage of said insertion needle through said catheter tube, said catheter tube having a restriction formed in the proximal portion thereof spaced apart from said hub so that said tube maintains its nominal inner diameter adjacent said hub, said restriction extends over a minor portion of the length of said catheter tube and provides a smaller radial gap between the inner wall of said catheter tube and the outer diameter of said corresponding insertion needle than exists between said inner wall of said catheter tube and said outer diameter of said insertion needle along said nominal inner diameter portion thereof.

2. The over-the-needle catheter assembly of claim 1, wherein said restriction is formed in the vicinity of the point of attachment of said catheter tube and said catheter hub.

3. The over-the-needle catheter assembly of claim 2, wherein the proximal end of the transition of the diameter of said tube from said restriction to said nominal tube diameter is spaced apart from the distal end of said catheter hub by approximately ⅛ inch.

4. The over-the-needle catheter assembly of claim 1, wherein said minor portion of the length of said catheter tube is approximately ¼ inch.

5. The over-the-needle catheter assembly of claim 1, wherein said smaller radial gap is in the range of 0.2 to 1,000 thousandths of an inch.

6. The over-the-needle catheter assembly of claim 5, wherein said smaller radial gap is approximately 0.5000 thousandths of an inch.

7. The over-the-needle catheter assembly of claim 1, wherein said restriction is thermally formed.

* * * * *